United States Patent [19]

Otto, deceased et al.

[11] 4,215,140
[45] Jul. 29, 1980

[54] CYANOMETHYL ALKYL TRITHIOCARBONATES AS INSECTICIDAL AGENTS

[75] Inventors: Julian A. Otto, deceased, late of Stockholm, N.J.; Ermalinda O. Cooke, administratrix, Ferguson, Mo.

[73] Assignee: Allied Chemical Corporation, Morristown, N.J.

[21] Appl. No.: 942,589

[22] Filed: Sep. 15, 1978

[51] Int. Cl.$^2$ .................. A01N 9/12; C07C 154/02
[52] U.S. Cl. ....................... 424/301; 260/455 R; 260/455 B
[58] Field of Search ................ 260/455 R, 455 B; 424/301

[56] References Cited

U.S. PATENT DOCUMENTS

| | | | |
|---|---|---|---|
| 2,600,737 | 6/1952 | Crouch et al. | 260/455 B |
| 2,820,807 | 1/1958 | Man | 260/455 R |

OTHER PUBLICATIONS

Noller, Textbook of Organic Chemistry, W. B. Saunders Company, Philadelphia, (1958), p. 209.
Reid, Organic Chemistry of Bivalent Sulfur, vol. IV, Chemical Publishing Co., Inc., New York, (1962), pp. 177–179.

*Primary Examiner*—Alan L. Rotman
*Assistant Examiner*—Robert C. Whittenbaugh
*Attorney, Agent, or Firm*—H. G. Jackson

[57] ABSTRACT

The invention is cyanomethyl alkyl $C_1$–$C_8$ trithiocarbonates which are effective in controlling adult dipterous insects.

8 Claims, No Drawings

CYANOMETHYL ALKYL TRITHIOCARBONATES AS INSECTICIDAL AGENTS

The invention is the compounds of the formula R—S—CS—SCH$_2$—CN wherein R is C$_1$-C$_8$ alkyl, a method for the preparation thereof and a method for controlling adults of dipterous insects by contacting the pests, their habitat or their food supply, with an adulticidally effective amount of the compound.

In accordance with this invention, cyanomethyl alkyl trithiocarbonate can be prepared by treating alkyl mercaptan with an alkali metal hydroxide or alkoxide in the presence of alcohol, ether especially tetrahydrofuran, hydrocarbon solvents or mixtures thereof followed by carbon disulfide to form the alkali metal alkyl trithiocarbonate which is then converted to the cyanomethyl alkyl trithiocarbonate by reaction with chloroacetonitrile.

This process for cyanomethyl methyl trithiocarbonate can be summarized as follows:

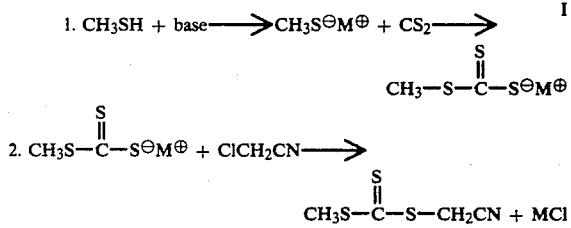

where M is an alkali metal and the base can be an alkali metal hydroxide or alkoxide.

The formation of the methyl trithiocarbonate salt is generally carried out at temperatures between about 0° and 30°. Although equimolar amounts of methyl mercaptan, alkali metal hydroxide or alkoxide and carbon disulfide are generally employed in the formation of the methyl trithiocarbonate salt, an excess of methyl mercaptan or carbon disulfide does not adversely affect the reaction. The salt is isolated by evaporation of the solvent.

This salt is dissolved in a ketone, such as methyl ethyl ketone, acetone, diethyl ketone, methyl isobutyl ketone or cyclohexanone and an approximately equimolar amount of chloroacetonitrile added to the reaction mixture. The mixture is stirred, allowed to cool to room temperature, and then concentrated in vacuo to give the crude cyanomethyl methyl trithiocarbonate. Treatment of the crude product with water and dichloromethane, followed by separation of the aqueous and organic phases and concentration of the organic phase gives cyanomethyl methyl trithiocarbonate which is further purified by distillation.

In addition it can be seen, by referring to the co-pending application of Peter John Wepplo and Donald Perry Wright filed Sept. 15, 1978 that the above-mentioned trithiocarbonate compounds have also been found to be effective ovicidal agents useful for the control of Lepodoptera, Coleoptera and Diptera.

Application of the compounds of the invention to insects and/or to the locus where the insects are found is generally facilitated by employing a composition containing an adulticidally effective amount of cyanomethyl alkyl trithiocarbonate in combination with an inert agricultural adjuvant. The compositions are conveniently prepared as wettable powders, flowable (thixotropic) concentrates, emulsifiable concentrates, dusts and the like.

In practice, these compositions are generally dispersed in water or other inexpensive liquid and applied as a dilute spray to the foliage and stems of plants sought to be protected against attack from the adult insects. However, these compositions may also be prepared as dusts or dust concentrates and applied with dusting equipment to the plants.

Dusts are generally prepared by grinding together about 10 to 25% by weight of the active ingredient and about 75% to 90% by weight of a finely divided solid carrier such as kaolin, attapulgite, wood flour or the like. Dust concentrates can be prepared in the same manner using from about 25% to 75% by weight of the active ingredient and 75% to 25% by weight of the solid adjuvant.

A typical emulsifiable concentrate which can be used in the above-mentioned spray applications is as follows:

Emulsifiable Concentrate

52% by weight—Cyanomethyl methyl trithiocarbonate
38% by weight —Cyclohexanone
10% by weight —Nonionic emulsifier.

When employed as an ovicidal agent, the emulsifiable concentrate will generally be dispersed in a sufficient quantity of water or other liquid to provide from about 0.04 ppm to 1000 ppm of active compound in solution. This dispersion is then generally applied at the rate of about 10 to 50 liters per hectare when applied with aerial application equipment or from about 50 to 1000 liters per hectare when applied with ground application equipment.

Flowable concentrates and wettable powders are applied in similar manner and at the same rates of application and concentration.

A typical flowable concentrate can be prepared by admixing 50% by weight of cyanomethyl methyl trithiocarbonate, 44% by weight of water, 4% by weight of sodium lignin sulfonate and 2% by weight of bentonite gelling clay.

When the compounds of this invention are used for the control of adult insects, it is generally desirable to use similar sprays. However, the concentration of active ingredient is preferably increased to between about 1000 ppm and 10,000 ppm. Such sprays are particularly effective for the control of adult Diptera when applied to the breeding and feeding grounds of the pests such as barns, stables, refuse and waste disposal areas, plant foliage, woodland, swamps, manure piles and the like.

Insect adults may also be controlled by mixing the compound of this invention with an attractant bait and placing the treated bait in the locus or habitat of the insects.

This invention is further illustrated by Examples set forth below.

EXAMPLE 1

Preparation of Potassium Methyl Trithiocarbonate

To 19.8 g of potassium hydroxide dispersed in 200 ml of absolute ethanol is added 16 g of methyl mercaptan. The mixture is stirred and maintained at from 10°–15° C. during the addition of the mercaptan. After a further 0.5 hours, 22.8 g carbon disulfide is added during 0.5 hours at 10–15° C. Stirring is continued for 3 hours at room temperature. The ethanol is stripped off under vacuum and 100 ml of dichloromethane is then added. A solid forms in the reaction mixture and is collected by filtering the mixture. The solid is then washed with dichloromethane and air dried to yield 30 g of product.

Analysis calculated for $C_2H_3S_3K$: C 14.8; H 1.85; S 59.0; Found: C 15.2; H 1.76; S 57.3.

EXAMPLE 2

Preparation of Cyanomethyl Methyl Trithiocarbonate

To 24.3 g of potassium methyl trithiocarbonate is added 200 ml of methyl ethyl ketone followed by 11.3 g of chloroacetonitrile. The mixture is stirred during admixture of these materials and stirring is continued for several days. The ketone is then stripped off under vacuum. The residue is treated with 100 ml of water and 100 ml of dichloromethane. The aqueous and organic layers are separated and the organic layer dried over $Na_2SO_4$ to give 24.5 g of crude product which is distilled to yield 17.5 g of oil, bp 115°–116° C. at 0.65 mm Hg.

Analysis calculated for $C_4H_5NS_3$: C 29.4; H 3.07; N 8.6; Found: C 29.9; H 3.04; N 10.2.

Following the above procedures of Examples 1 and 2 the appropriate mercaptan yields the following products:

Cyanomethyl ethyl trithiocarbonate, bp 115°–117° C./0.2 mm Hg;

Cyanomethyl propyl trithiocarbonate, bp 115°–119° C./0.25 mm Hg;

Cyanomethyl butyl trithiocarbonate, bp 131°–138° C./0.25 mm Hg;

Cyanomethyl sec-butyl trithiocarbonate, bp 112°–118° C./0.1 mm Hg;

Cyanomethyl isobutyl trithiocarbonate, yellow oil

Cyanomethyl pentyl trithiocarbonate, bp 129°–131° C./0.1 mm Hg;

Cyanomethyl tert-pentyl trithiocarbonate, yellow oil;

Cyanomethyl heptyl trithiocarbonate, bp 149°–151° C./0.1 mm Hg;

Cyanomethyl heptyl trithiocarbonate, bp 150° C./0.05 mm Hg;

Cyanomethyl octyl trithiocarbonate, yellow oil.

EXAMPLE 3

Preparation of Cyanomethyl Isopropyl Trithiocarbonate

To a two phase system containing 100 ml of water, 100 ml of toluene, 19.0 g (100 mmol) of potassium isopropyl trithiocarbonate and 50 mg of tetrabutyl ammonium bisulfate, a phase transfer catalyst, is added 6.3 ml (100 mmol) of chloroacetonitrile. The temperature of the reaction is maintained at between 20° and 30° C. After 4.5 hours the layers are separated and the toluene layer washed with water, brine, dried with $Na_2SO_4$, filtered, and concentrated in vacuo. The residue is distilled to give 11.4 g of isopropyl cyanomethyl trithiocarbonate as a yellow oil, boiling point 110°–113° C. at 0.1 mm Hg.

EXAMPLE 4

Evaluation of test compounds for control of adult house flies (*Musca domestica*)

Three to four day old flies are caged 50/cage, mixed sexes. They are supplied with a formulated bait of 1:1 sugar:nonfat dry milk containing 1000 ppm of cyanomethyl methyl trithiocarbonate and a water supply in a cage consisting of a 4-liter glass battery jar covered with a screen lid. Oviposition media is supplied in the cages when flies are 8-9 days old. Eggs are usually found 10 days after flies emerge if the flies are not killed by the test composition. The oviposition media is checked daily for the presence of eggs, and is replaced daily if eggs appear. During the 10 day test period the cages are held in a room at 27° C.

In these tests flies receiving the test composition containing 1000 ppm of cyanomethyl methyl trithiocarbonate all died without laying any eggs. Controls receiving untreated sugar:non-fat dry milk were alive and laid eggs.

EXAMPLE 5

Evaluation of test compounds for control of adult house flies (*Musca domestica*)

Dry food (6 parts powdered non-fat dry milk and 6 parts granulated sugar) is treated with chemical in acetone solution, suspension or wettable powder. Solutions or suspensions are added to the dry food and allowed to dry then repulverized. Wettable powders are mixed with the dry food with the aid of mortar and pestle. The treated food is placed in emergence cages containing 50 3-4 day old flies. Cages containing untreated food are used as checks. Examination of each cage is made periodically to determine condition of flies, and acute toxicity. Nine days after start of test, oviposition medium is placed in each cage and on the following day the medium is examined for eggs and if none are present the medium is moistened and examined daily until oviposition occurs or all adults are dead. Egg viability is determined by inspecting the medium for growing larvae 2-3 days after oviposition. The results are reported in Table I.

TABLE I

| R-S-CS-SCH$_2$CN | Concentration | % Kill of Adult Flies | | | | Egg Hatch at 7 Days, Larvae at 11 Days |
| --- | --- | --- | --- | --- | --- | --- |
| | | 1 Day | 3 Days | 5 Days | 7 Days | |
| R = CH$_3$ | 1.0% | 100 | | | | No eggs. |
| | 0.1 | 100 | | | | No eggs. |
| | .01 | 2 | 12 | 26 | 32 | Good Hatch, Many Larvae. |
| R = C$_2$H$_5$ | 1.0% | 100 | | | | No eggs. |
| | 0.1 | 100 | | | | No eggs. |
| | .01 | 2 | 12 | 12 | 18 | Good Hatch, Many Larvae. |
| R = n-C$_3$H$_7$ | 1.0% | 100 | | | | No eggs. |
| | 0.1 | 100 | | | | No eggs. |
| | .01 | 26 | 66 | 84 | 92 | Good Hatch, Few Larvae. |
| Check | — | 2 | 2 | 6 | 14 | Good Hatch, |

TABLE I-continued

| R-S-CS-SCH$_2$CN | Concentration | % Kill of Adult Flies | | | | Egg Hatch at 7 Days, Larvae at 11 Days |
|---|---|---|---|---|---|---|
| | | 1 Day | 3 Days | 5 Days | 7 Days | |
| | | | | | | Many Larvae |

What is claimed is:

1. A compound of the formula:

$$R-S-CS-SCH_2-CN$$

wherein R is alkyl $C_1$–$C_8$.

2. A compound according to claim 1 cyanomethyl methyl trithiocarbonate.

3. A compound according to claim 1 cyanomethyl ethyl trithiocarbonate.

4. A compound according to claim 1 cyanomethyl n-propyl trithiocarbonate.

5. A method for the control of dipterous insects, comprising applying to the insects, to their habitat or food supply, an adulticidal amount of a compound of the formula $R-S-CS-SCH_2-CN$ wherein R is alkyl $C_1$–$C_8$.

6. A method according to claim 5 wherein the compound is cyanomethyl methyl trithiocarbonate.

7. A method according to claim 5 wherein the compound is administered to dipterous insects in their food supply in an amount sufficient to supply about 1000 ppm of the trithiocarbonate in the food supply.

8. A method according to claim 5 wherein the compound is applied to the insects or their habitat in the form of a liquid spray containing from about 1000 to 10,000 ppm of cyanomethyl methyl trithiocarbonate.

* * * * *